US007118210B2

(12) United States Patent
Landers (10) Patent No.: US 7,118,210 B2
(45) Date of Patent: *Oct. 10, 2006

(54) EYE COVERS (76) Inventor: Luke E. Landers, 1689 Benedict Ave., Claremont, CA (US) 91711

( * ) Notice: Subject to any disclaimer, the term of this patent is extended or adjusted under 35 U.S.C. 154(b) by 0 days.

This patent is subject to a terminal disclaimer.

(21) Appl. No.: 11/284,748

(22) Filed: Nov. 22, 2005

(65) Prior Publication Data

US 2006/0072068 A1 Apr. 6, 2006

Related U.S. Application Data (63) Continuation-in-part of application No. 10/667,839, filed on Sep. 22, 2003, now Pat. No. 7,004,581.

(51) Int. Cl.
G02C 5/14 (2006.01)
(52) U.S. Cl. .......................... 351/123; 351/41; 351/111
(58) Field of Classification Search ................ 351/123, 351/111, 41; 2/448, 12
See application file for complete search history.

(56) References Cited

U.S. PATENT DOCUMENTS

| 1,562,319 | A | * | 11/1925 | Fairall | ........................... 2/454 |
| 4,649,908 | A | * | 3/1987 | Ghaly | ......................... 128/858 |
| 4,886,349 | A | * | 12/1989 | Willis | .......................... 351/111 |
| 5,719,655 | A | * | 2/1998 | Peschel et al. | .............. 351/111 |
| 6,557,994 | B1 | * | 5/2003 | Rose | ............................ 351/41 |
| 6,984,037 | B1 | * | 1/2006 | Bleau | ........................... 351/83 |
| 7,004,581 | B1 | * | 2/2006 | Landers | ....................... 351/41 |

FOREIGN PATENT DOCUMENTS

DM 036821 8/1995

* cited by examiner

Primary Examiner—Hung Xuan Dang
(74) Attorney, Agent, or Firm—Notaro & Michalos P.C.

(57) ABSTRACT

An eye cover for use as sunglasses, eye shields, eye glasses or other eye wear, is formed of an elongated and flexible sheet of transparent plastic material adapted to extend horizontally over both eyes and temples of a wearer, to a location forward of the ears of the wearer. The sheet has a central nose engaging area, a pair of viewing areas on opposite sides of the nose engaging area and a pair of temple engaging areas each extending from one of the viewing areas. Each of the temple areas have inner surfaces and are bent for use into an arcuate position with the inner surfaces engaging the temples of a wearer. A bend retaining mechanism, such as wires connected to the perimeter of the sheet, form and resiliently maintain the arcuate position of each of temple area.

23 Claims, 5 Drawing Sheets

EYE COVERS

CROSS REFERENCE TO RELATED APPLICATION

This is a continuation-in-part of application Ser. No. 10/667,839 filed Sep. 22, 2003 now U.S. Pat. No. 7,004,581 entitled EYE COVERS, and incorporated here by reference.

FIELD AND BACKGROUND OF THE INVENTION

The present invention relates generally to the field of eye wear, and, in particular, to a new and useful, light weight eye covers with no ear engaging temples, which can be used as sunglasses, eye shields, eyeglasses or the like.

Conventional eye wear utilizes either a frame or frameless structure that includes means for suspending transparent viewing areas in front of the eyes of the wearer. This part of the eye wear is usually supported on the bridge of the nose. Conventional eye wear also includes side pieces commonly referred to as "temples" which are designed to extend along the side of the face and over the ears.

Alternate approaches for supporting eye wear on the head of a user include bands and cords which extend entirely around the user's head.

Several attempts have also been made to provide eye wear with no temples. See, for example, U.S. Pat. No. 1,562,319 to Fairall which discloses simplified eye wear made of a pair of slidably engaged plastic sheets having side portions that can be bent to engage the wearer's temple, forward of the wearer's ears.

The eye wear is, thus, made lightweight and engages the temples at relatively sharp ridges. The eye wear is held to the head by friction between the sharp ridge and the temples of the wearer.

U.S. Pat. No. 3,419,909 to Spain also discloses temple-less eye wear. Side pieces engage the temples of the wearer by friction. The frame is permanently formed into a U-shape for this purpose.

Another approach to temple-less eye wear is disclosed in U.S. Pat. No. 4,837,862 to Heil. In this case, suction cups or adhesive tapes are used to engage the temples of the wearer, forward of the wearer's ears, to hold the viewing areas of the eye wear in front of the eyes of the user.

U.S. Pat. No. 5,719,655 to Paschel, et al discloses temple-less eye wear using magnets to engage adhesively attached magnets or magnetically attractable areas at the temples of the user. Also see U.S. Pat. No. 715,533 to Anderson (1902) and U.S. Pat. No. 714,664 to Briggs (1902) for eye wear having temple engaging structures.

U.S. Pat. No. 4,886,349 to Willis, discloses temple-less eye wear having cushions for frictionally engaging the wearer's temples to hold the eye wear to the wearer's head.

A simplified light weight eye wear structure is also disclosed by U.S. Pat. No. 3,614,216 to Rosenthal. A sheet of resilient flexible plastic that includes viewing areas is preformed into a curled shape. Even when uncurled, the material of the sheet has "memory" and tries to return to its curled state. By using this attribute, a wearer uncurls the specially shaped sheet of material and then engages it to his or her head. The sides of the sheet material, which is constantly trying to return to its curled state, closely engages the temple areas of the wearer, forward of the ears, and thus, holds the eye wear to the wearer's head. This structure, however, applies continuous firm pressure to the temples of the wearer. This pressure, as with the disclosure of U.S. Pat. No. 1,562,319 to Fairall, is concentrated at a sharp ridge or edge against the sides of the head and may result in headaches. Certainly, long wear of this type of structure would be uncomfortable. Further, none of the known structures are made of material or incorporate means which allow bending of at least the temple areas into a smooth arcuate shape, which shape is retained and sufficiently fixed to allow smooth flat surfaces to gently press against the surfaces of the wearer's temples, forward of the wearer's ears, to hold the eye wear with its viewing areas in front of the wearer's eyes.

SUMMARY OF THE INVENTION

Accordingly, an object of the present invention is to provide ultra simple and ultra lightweight eye wear that can be used as a basis for sunglasses, eye shields and even eye glasses.

The sunglasses or more generally, the eye wear, or simply eye cover of the invention preferably comprises a single piece of flexible transparent material which, when bent, retains its bent shape until and so far as it is bent and formed into another shape (whether flatter or more curved).

The mechanism by which the eye cover achieves this quality of bendability is not limited to one single mode of construction or type of material. That is, the invention applies to any and all products which serve as eye wear having the property of "shape-to-fit" flexibility and malleability.

One embodiment of the invention achieves this shape-to-fit capability by means of a wire attached to the perimeter region of the flexible transparent material. It is also possible to use a material which inherently possesses the property of shape memory and of shape reversibly, hence avoiding the need for a wire or similar flexible metal piece.

For a construction utilizing wire, it is preferable, but not necessary, that the wire be embedded into the flexible transparent material itself. Furthermore, the wire need not run around the entire perimeter of the flexible transparent material. For example, a single piece of wire provided along the top perimeter can achieve the desired effect, or three different wire pieces can be incorporated—one running along the top and two shorter wires running along the bottom right and left sides of the invention.

The overall shape of a product made according to the invention is not restricted to a single design or limited number of designs. That is, the product can be wider, narrower, longer and shorter, symmetrical or asymmetrical.

One non-limiting example of the form of the invention is oval and extends about two-thirds along the temple or side of the head to the ear, and provides an allowance, e.g. a notch, in the shape for the bridge of the wearer's nose.

The basic distinctiveness of the invention is that it has the capacity to be bent from one shape (e.g. flat) to another shape (e.g. curved), to retain that shape, and then to be bent into another shape, all on its own, without recourse to an extraneous structures such as a band (elastic or otherwise) attached to the ends and extending around the head or conventional ear-supported "temples."

Further distinctions of the invention resides in the fact that a heretofore unachieved level of comfort is made possible since a product of the invention can be shaped so as to apply the tension requisite for holding the product on the face, in a uniform manner along a maximum surface of the sides, thus, any sort of localized pressure point on the nose, ears, etc., can be avoided.

Further distinctiveness resides in the fact that the product, having eliminated the need for the side arm supports or conventional "temples" extending past the ears, is capable of being much more lightweight than other eye wear.

Further advantage resides in the easy storing a product which is afforded to it by its bendability. Unlike other eye wear, the product can be made to be flat so that it can be stored in a minimal thin space.

Accordingly, a further object of the invention is to provide an eye cover comprising: an elongated and flexible sheet of material adapted to extend horizontally over both eyes and temples of a wearer, to a location forward of the ears of the wearer, the sheet having a central nose engaging area, a pair of viewing areas on opposite sides of the nose engaging area, and a pair of temple engaging areas each extending from one of the viewing areas, at least the viewing areas being transparent, each of the temple engaging areas having inner planar surfaces and being bent for use by the wearer, into an arcuate position with the inner flat surfaces engaging the temples of the wearer at a location forward of the ears of the wearer, each temple engaging area having a flat storage position lying in a common plane with the nose engaging area and viewing areas of the sheet; and bend retaining means located at least at a perimeter of the temple engaging areas for being bent to form and resiliently maintain the arcuate position of each of the temple engaging areas, and for being bent to form and maintain the storage position of each temple engaging area.

It is noted that the smooth plastic inner surfaces of the temple engaging areas that flatly and gently press against the wearer's temples, adhere slightly to the wearer's skin, due to the slightly moist content of skin and the tendency of smooth plastic to "stick" to the skin. This slight adhesion is enough to support the sides of the eye cover on the face due to the extremely light weight nature of the inventive eye cover. The center of the eye cover is supported on the bridge of the nose, whether a concave nose notch is provided or not.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
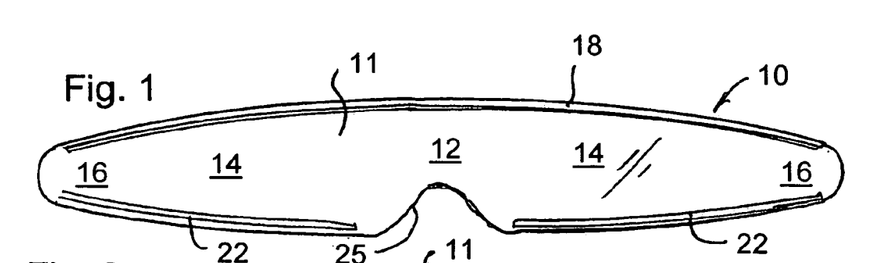
FIG. 1 is a front elevational view of an eye cover illustrating one embodiment of the invention.

Referring now to the drawings, in which like reference numerals are used to refer to the same or similar elements, the invention embodied in FIG. 1 comprises an eye cover generally designated 10, which can be tinted or provided in a color to act as sunglasses, or be clear to act as eye shields, or be provided with optical characteristics to form corrective eye glasses.

Figure 8:
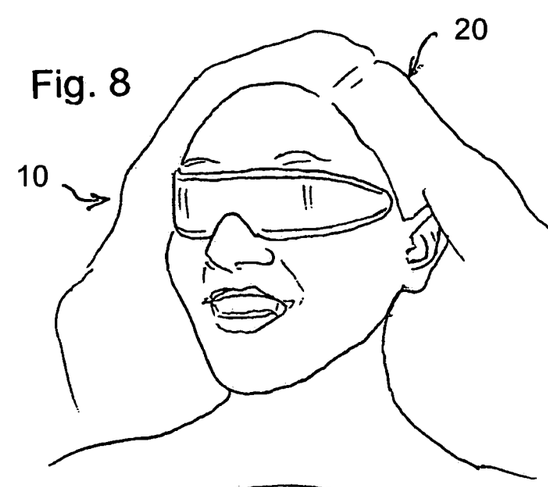
FIG. 8 is a perspective view of an embodiment of the eye cover of the invention as it appears while being worn by a user of the invention.

The eye cover 10 advantageously comprises a single elongated and flexible sheet of material 11, adapted to extend horizontally over both eyes and temples of a wearer 20 in FIG. 8, to a location forward of the ears of the wearer.

Referring back to FIG. 1, the sheet has a central nose engaging area 12, a pair of viewing areas 14 on opposite sides of the nose engaging area 12, and a pair of temple engaging areas 16 each extending from one of the viewing areas 14. At least the viewing areas 14 are transparent, although in a preferred form of the invention, the entire sheet is transparent although all of the sheet may be in a dark color if the eye cover is to be used as sunglasses.

Figure 3:
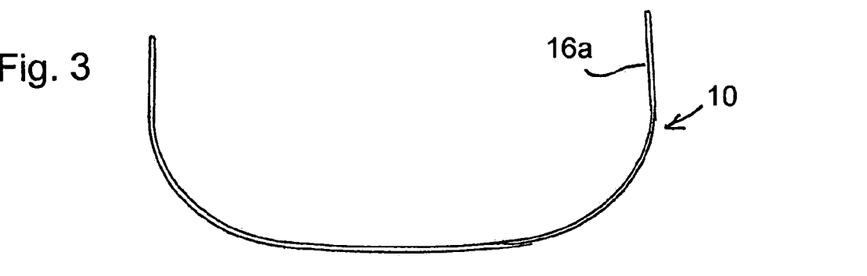
FIG. 3 is a top plan view of an eye cover of the invention, bent into a position for use.

Each of the temple engaging areas 16 has an inner, preferably smooth planar surface 16*a* in FIG. 3, and is bent for use by the wearer, into an arcuate position shown in FIG. 3, with the inner flat surfaces engaging the temples of the wearer at locations spaced forwardly of the ears as shown in FIG. 8. Each temple engaging area 16 also has a flat storage position shown in FIG. 1, lying in a common plane with the nose engaging area 12 and viewing areas 14, of the sheet.

Bend retaining means are located at least at a perimeter of the temple engaging areas for being bent to form and resiliently maintain the arcuate position of each of the temple engaging areas 16, and for being bent to form and maintain the storage position of each temple engaging area.

Figure 4:
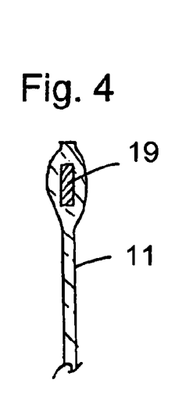
FIG. 4 is a partial, sectional view of an embodiment of the present invention showing one bend retaining mechanism therefore.
Figure 5:
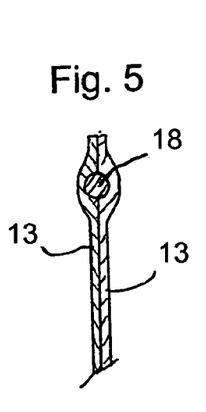
FIG. 5 is a partial, sectional view of another embodiment of the present invention showing a further bend retaining mechanism therefore.
Figure 6:
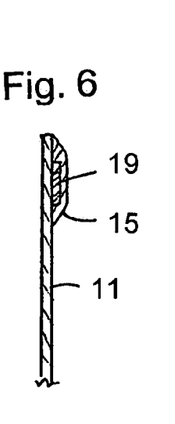
FIG. 6 is a view similar to FIG. 4 of a further embodiment for the bend retaining mechanism.
Figure 7:
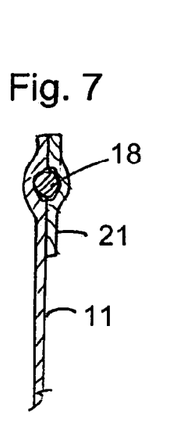
FIG. 7 is a view similar to FIG. 4 of a still further embodiment for the bend retaining mechanism.

Although the eye cover is preferably a single sheet of transparent plastic material, the material can have one or more than one layer. The bend retaining means comprises, for example, a reversibly bendable wire 18, 22, intimately connected along at least part of the perimeter of the viewing areas 14 and the temple engaging areas 16. As shown in FIGS. 5 and 7, the wire 18 may have a circular cross-section, or as shown in FIGS. 4 and 6, the wire 19 in these figures, may have a rectangular cross-section.

The intimate connection may be by embedding the wire or wires into the material thickness of the sheet material 11 (FIG. 4), or providing the wire(s) between two full area layers 13,13 of the sheet material of the eye cover (FIG. 5), or embedding the wire(s) in a bead of adhesive 15 (FIG. 6), or sealing the wire(s) under a border of plastic material 21 (FIG. 70), or in any other way is consistent with the other features of the invention.

The plastic material can be any one or more or of any suitable thermoplastic, for example, or other plastic suitable to the purpose of the invention.

Examples include: (i) a high or low density poly ethylene (HDPE, LDPE), or (ii) a transparent and flexible plasticized polyvinyl chloride, or (iii) a cellulose acetate, or (iv) a clear and flexible polyamide, etc.

The plastic sheet material used for the invention should be in the thickness range of about 7 to 30 thousandths of an inch (~0.007"–0.030").

The wire 18, 19, 22, may be some variety of stainless steel alloy (containing various amounts of chromium, nickel, manganese and/or silicon) or a variety of nickel titanium; or a copper alloy (e.g. silver plated), or a nickel-free titanium alloy (e.g. "BTA" Bendable Titanium Alloy), or some variety of aluminum alloy. Understanding the principles of the invention, the person of ordinary skill in this art can select suitable metal for the wire of the eye cover.

Figure 2:
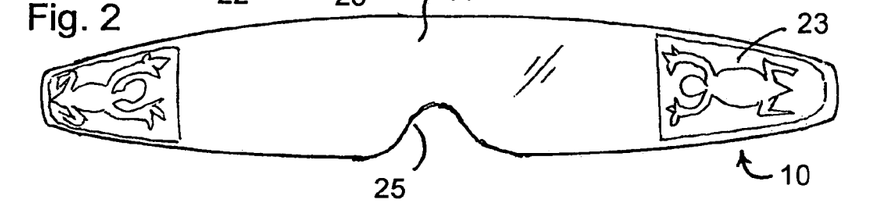
FIG. 2 is a front elevational view of a second embodiment of the invention.

The bend retaining means of the eye cover of the invention may simply be the plastic material itself if it can be reversibly bent to form the resilient arcuate curved positions of the temples as shown in FIG. 2.

As also shown in FIG. 3, the curve of the arcuate positions of the temple engaging areas can extend into the viewing areas and even into the nose engaging areas, to create a continuous and graceful arc for engaging the wearer's face as shown in FIG. 8.

Figure 9:
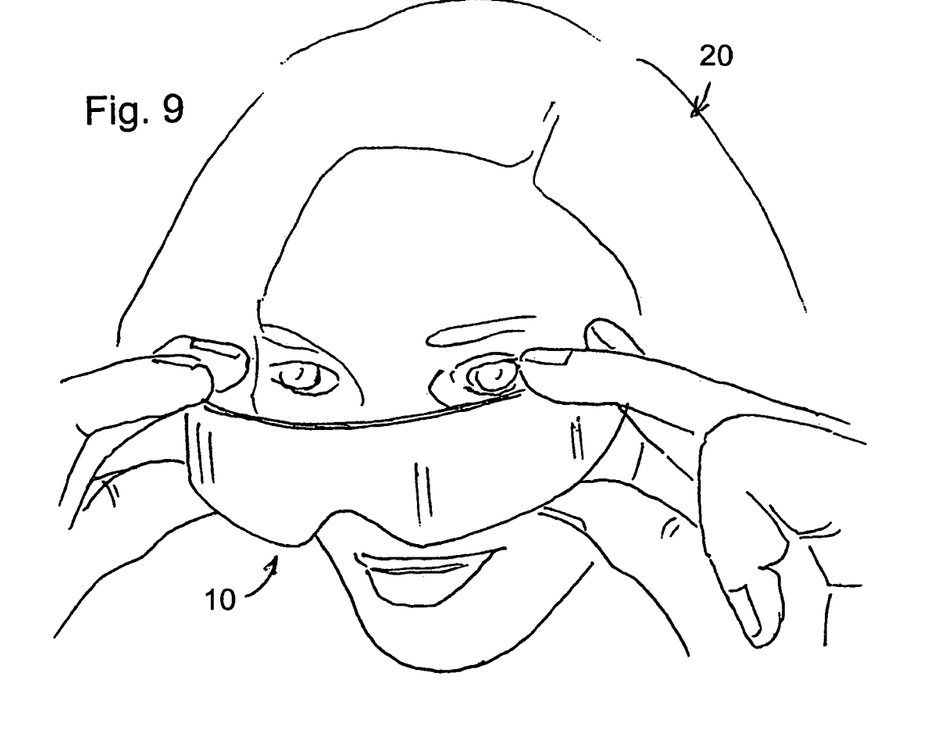
FIG. 9 is a perspective view of an embodiment of the eye cover of the invention as it is being put on by a user of the invention.

As shown in FIG. 9, after having bent the eye cover into the arcuate positions of FIG. 3 for the temple engaging areas, the wearer uses the hands to spread the eye cover slightly and places the temple engaging areas of her or his temples. By then releasing the eye cover, the inner surfaces of the temple engaging areas comes to rest against the wears skin at the temples and is held there, gently to avoid pressure that may cause a headache, but securely due to the natural adhesion of smooth plastic to human skin.

As illustrated in FIG. 2, graphic layers 23 may be provided at least at one of the nose engaging, viewing and temple engaging areas. This can be by screen printing or other printing in the inner and/or outer surfaces of the sheet 11, or by embedding graphics between two layers 13,13 making up the sheet, or by other means. The graphics may be of the type which is transparent to the wearer but at least partly opaque when viewed from an outer surface of the eye cover. This can be done by making the graphic layer very thin or by providing a multitude of closely spaced perforations in the graphic layer. This will allow the wearer to see through the graphics even while the graphics seem to be opaque for the outside.

The eye cover 10 with its nose engaging, viewing and temple engaging areas, togetherform a smoothly curving generally oval perimeter shown in FIGS. 1 and 2. The bend retaining means comprised the reversibly bendable wire 18 intimately connected to the sheet 11 along a smoothly convexly curved upper portion of the perimeter of the sheet, and the likewise reversibly bendable wires 20 are at the lower portions of the perimeter, spaced from a concave nose notch 25 in the nose engaging area, which is present in the embodiments of FIGS. 1 and 2, to support the eye cover at the bridge of the wearer's nose, but is not essential. Other shapes are also possible for the sheet 11.

Because the eye cover of the invention is so light weight the temple engaging areas tend to stick to the skin of the wearer to support the temple engaging areas and the sides of the eye cover, at the temples of the wearer.

Referring now to the embodiment of FIGS. 10 to 14, the eye cover 10 comprises an elongated and flexible sheet of material 11 adapted to extend horizontally over both eyes and temples of a wearer, to a location forward of the ears of the wearer as in FIG. 8, the sheet having a central nose engaging area, a pair of viewing areas on opposite sides of the nose engaging area, and a pair of temple engaging areas each extending from one of the viewing areas as in the embodiment of FIG. 1. At least the viewing areas, but preferably all of the sheet 11, is transparent. The flexible sheet of material is bent for use by the wearer, into an arcuate position with the temple engaging areas over temples of the wearer, at a location forward of the ears of the wearer also as in FIG. 8.

Figure 12:
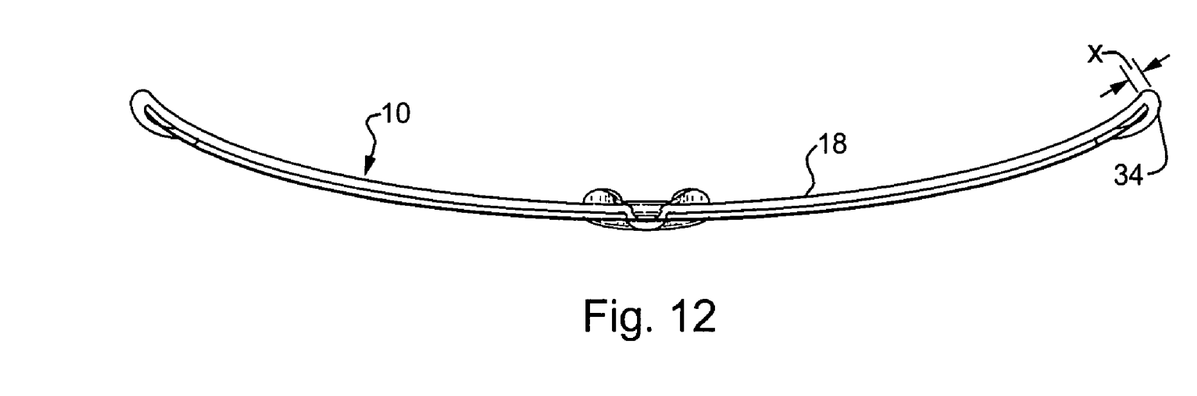
FIG. 12 is a top plan view of the embodiment of FIG. 10.
Figure 13:
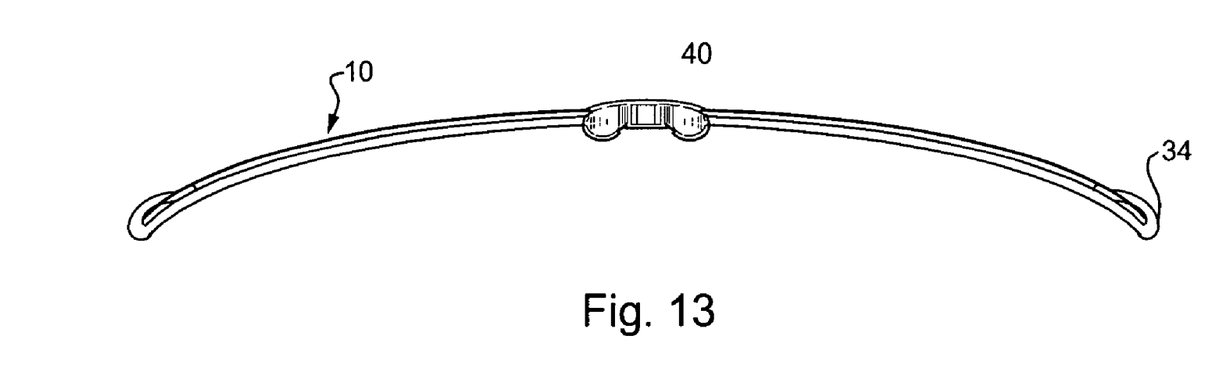
FIG. 13 is a bottom plan view of the embodiment of FIG. 10.
Figure 14:
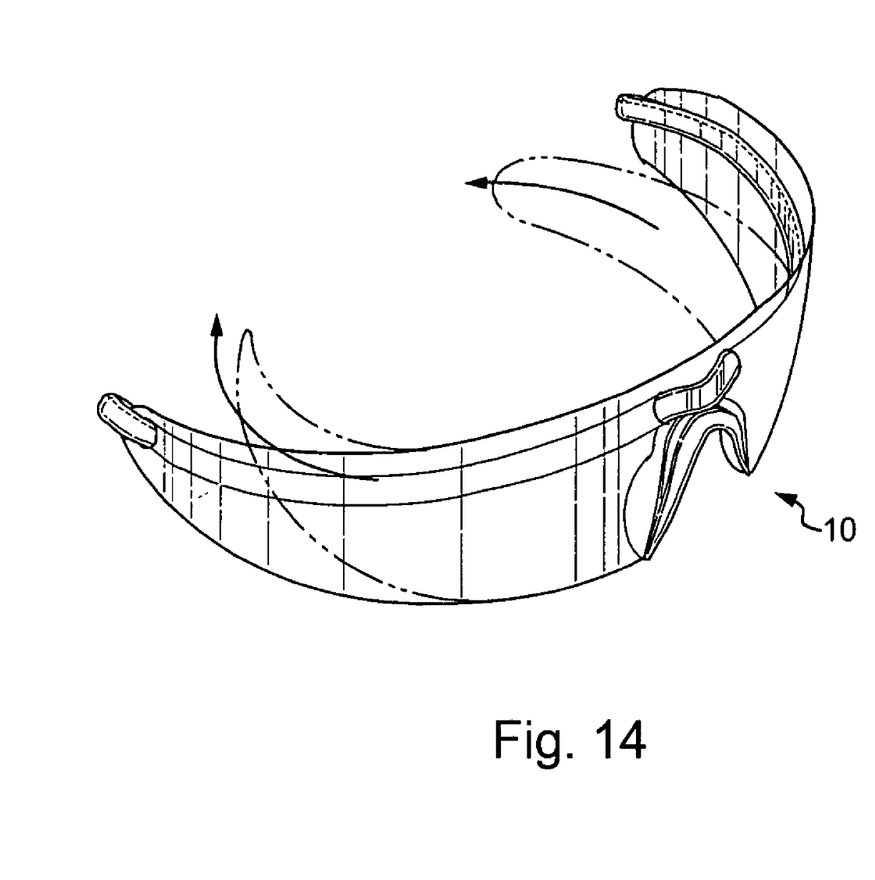
FIG. 14 is a perspective view of the embodiment of FIG. 10 as it is being bent to shape for use.

In FIGS. 12 and 13, a bendable wire generally designated 18 is shown engaged to the flexible sheet of material 11 and extends across the pair of viewing areas, the nose engaging area and the pair of temple engaging areas, near an upper edge of the flexible sheet of material for being bent to form, and resiliently maintain, the arcuate position, and for being bent to form and maintain a storage position of the flexible sheet of material which is flatter than the arcuate position. FIGS. 12 and 13 show the flattened storage position and FIG. 14 shows the action of bending the eye cover into its arcuate use position.

Figure 11:
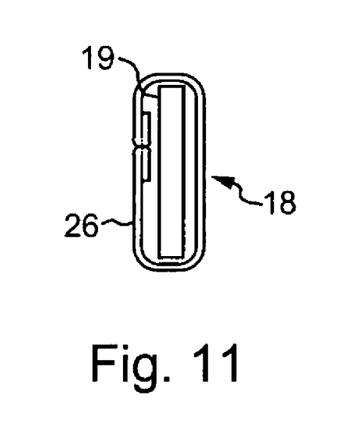
FIG. 11 is an enlarged side view of a covered bendable metal ribbon used in the embodiment of FIG. 10.

The wire 18 is preferably a flat cross-sectioned, untempered ribbon 19 as best shown in FIG. 11, covered by a flexible fabric, real or imitation leather, Neoprene (a trade name for a family of synthetic rubbers based on polychloroprene) or other like material tube of material 26. The tube can be sewn or otherwise closed alone its length into the tubular shape for covering the wire ribbon 19. The use of untempered metal, such as iron, brass, bronze, aluminum, or alloys thereof, or other metal, allows the arcuate shape to be bent into form and keep that shape. Some resilience is needed only to help press the ends of the covered wire against the wearer's temples to hold the eye cover in place over the wearer's eyes. The wire can alternatively be made of a bendable plastic or a covered or composite plastic or plastic and metal ribbon.

Figure 10:
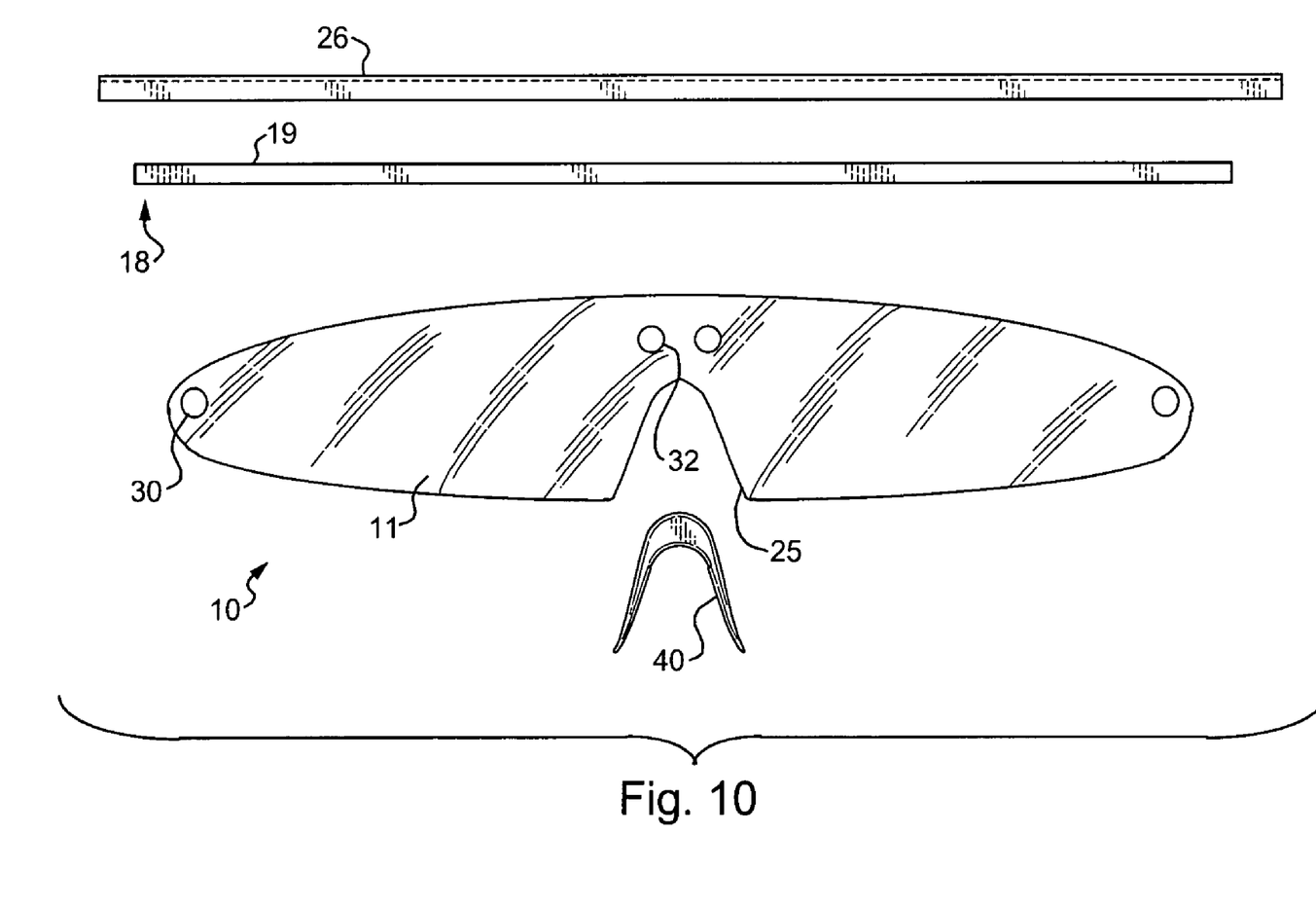
FIG. 10 is an exploded view of a further embodiment of the invention.

The flexible sheet of material 11 includes a plurality of apertures 30 and 32 shown best in the exploded view of FIG. 10, and the bendable wire 18 is engaged to the flexible sheet of material by being woven through the apertures as shown in FIGS. 12 and 13. Although adhesive can be used to hold the wire to the sheet, this is not necessary because of the placement of the apertures and nature of the wire. The flexible sheet of material preferably includes a pair of apertures 32 at an upper portion of the nose engaging area over a nose receiving notch 25, and an aperture 30 near the outer end of each temple engaging area. The bendable wire is engaged to the flexible sheet of material by being woven through the apertures with opposite ends of the wire being bent at 34 from an inner, to an outer surface of each temple engaging area, around a respective end of each temple engaging area and into an aperture 30 at the end of the respective temple engaging area with a clearance X between an inside of the wire bend and the end of each temple engaging area. This allows the wire 18 to slide with respect to the flexible sheet of material 11 when the flexible sheet of material is moved between the arcuate and storage positions (FIG. 14). This sliding is needed to compensate for the different arcuate length of the wire 18 and sheet of material 11, as the eye cover is bent.

A slotted nose guard 40 can also be adhered to the nose notch 25 for increased comfort to the wearer.

Also, by extending the wire 18 over a substantial portion of the inner surface of the viewing areas, the covered wire engages the wearer's face to help space the sheet material 11 from the eyes and acts as a sweat band as well. Bending the wire 18 through the apertures 32, places the wire outside the sheet 11 in the nose area, helps avoid the bridge of the wear's nose and fixes the middle of the wire to the sheet, in a simple and elegant manner, without adhesive and while still allowing the opposite ends of the wire to slide with respect to the sheet 11.

While specific embodiments of the invention have been shown and described in detail to illustrate the application of the principles of the invention, it will be understood that the invention may be embodied otherwise without departing from such principles.

What is claimed is:

1. An eye cover comprising: an elongated and flexible sheet of material adapted to extend horizontally over both eyes and temples of a wearer, to a location forward of the ears of the wearer, the sheet having a central nose engaging area, a pair of viewing areas on opposite sides of the nose engaging area, and a pair of temple engaging areas each extending from one of the viewing areas, at least the viewing areas being transparent, each of the temple engaging areas having inner planar surfaces and being bent for use by the wearer, into an arcuate position with the inner flat surfaces adjacent the temples of the wearer at a location forward of the ears of the wearer, each temple engaging area having a substantially flat storage position lying in a common plane with the nose engaging area and viewing areas of the sheet; and bend retaining means located at least at part of a perimeter of the temple engaging areas for being bent to form, and resiliently maintain the arcuate position of each of the temple engaging areas, and for being bent to form and maintain the storage position of each temple engaging area.

2. The eye cover of claim 1, wherein the sheet of material is a single sheet of transparent plastic material, the bend retaining means comprising a reversibly bendable wire, intimately connected along at least part of the perimeter of the viewing areas and the temple engaging areas.

3. The eye cover of claim 1, wherein the sheet of material is a single sheet of transparent plastic material, the bend retaining means comprising a reversibly bendable wire, intimately connected along at least part of the perimeter of the viewing areas and the temple engaging areas, and having a circular cross-section.

4. The eye cover of claim 1, wherein the sheet of material is a single sheet of transparent plastic material, the bend retaining means comprising a reversibly bendable wire, intimately connected along at least part of the perimeter of the viewing areas and the temple engaging areas, and having a rectangular cross-section.

5. The eye cover of claim 1, wherein the sheet of material is a single sheet of transparent plastic material, the bend retaining means comprising a reversibly bendable wire, intimately connected along at least part of the perimeter of the viewing areas and the temple engaging areas; plastic material being at least one thermoplastic selected from: a high or low density poly ethylene; a transparent and flexible plasticized polyvinyl chloride; a cellulose acetate; or a clear and flexible polyamide; and having a thickness of about 7 to 30 thousandths of an inch; and the wire being made of at least one of: stainless steel alloy containing amounts of at least one of chromium, nickel, manganese or silicon; nickel titanium; copper alloy; nickel-free titanium alloy; bendable titanium alloy; or aluminum alloy.

6. The eye cover of claim 1, wherein the sheet of material is a single sheet of transparent plastic material, the bend retaining means comprising the plastic material being reversibly bendable material.

7. The eye cover of claim 1, wherein the sheet of material is a single sheet of transparent plastic material, the bend retaining means comprising the plastic material being reversibly bendable material and being a thermoplastic.

8. The eye cover of claim 1, wherein the sheet of material is a single sheet of transparent plastic material having a graphics layer at least at one of the nose engaging, viewing and temple engaging areas.

9. The eye cover of claim 1, wherein the sheet of material is a single sheet of transparent plastic material having a graphics layer at least at one of the nose engaging, viewing and temple engaging areas which is transparent to the wearer but at least partly opaque when viewed from an outer surface of the eye cover.

10. The eye cover of claim 1, wherein the nose engaging, the viewing and the temple engaging areas together form a smoothly curving generally oval perimeter, the bend retaining means comprising a reversibly bendable wire intimately connected to the sheet, at least along part of the perimeters of the temple engaging areas.

11. The eye cover of claim 1, wherein the nose engaging, the viewing and the temple engaging areas together form a smoothly curving generally oval perimeter, the bend retaining means comprising a reversibly bendable wire intimately connected to the sheet, at least along parts of upper and lower perimeters of the viewing areas and the temple engaging areas.

12. The eye cover of claim 1, wherein the nose engaging, the viewing and the temple engaging areas together form a smoothly curving generally oval perimeter having a smoothly convexly curved upper portion and a lower portion with a concave nose notch in the nose engaging area, the bend retaining means comprising reversibly bendable wires intimately connected to the sheet and extending along the upper portion of the oval perimeter and along the lower portion of the oval perimeter away from the nose notch.

13. The eye cover of claim 1, wherein the nose engaging, the viewing and the temple engaging areas together form a smoothly curving generally oval perimeter having a smoothly convexly curved upper portion and a lower portion with a concave nose notch in the nose engaging area, the bend retaining means comprising reversibly bendable wires intimately connected to the sheet and extending along the upper portion of the oval perimeter and along the lower portion of the oval perimeter away from the nose notch, each temple engaging area having an outer convexly curved perimeter with no wire extending there-along.

14. The eye cover of claim 1, wherein the sheet of material is a single sheet of transparent plastic material having an inner surface including the inner surfaces of the temple engaging areas, which is smooth and tends to stick to the skin of the wearer to support the temple engaging areas at the temples of the wearer.

15. An eye cover comprising: an elongated and flexible sheet of material adapted to extend horizontally over both eyes and temples of a wearer, to a location forward of the ears of the wearer, the sheet having a central nose engaging area, a pair of viewing areas on opposite sides of the nose engaging area, and a pair of temple engaging areas each extending from one of the viewing areas, at least the viewing areas being transparent, the flexible sheet of material being bent for use by the wearer, into an arcuate position with the temple engaging areas over temples of the wearer, at a location forward of the ears of the wearer; and a bendable wire engaged to the flexible sheet of material and extending across the pair of viewing areas, the nose engaging area and the pair of temple engaging areas, near an upper edge of the flexible sheet of material for being bent to form, and to resiliently maintain, the arcuate position, and for being bent to form and maintain a storage position of the flexible sheet of material which is flatter than the arcuate position.

16. The eye cover of claim 15, wherein the flexible sheet of material includes a plurality of apertures and the bendable wire is engaged to the flexible sheet of material by being woven through the apertures.

17. The eye cover of claim 15, wherein the flexible sheet of material includes a plurality of apertures and the bendable wire is engaged to the flexible sheet of material by being woven through the apertures, the wire extending along inner surfaces of the viewing areas and the temple engaging areas for engaging the wearer and for spacing the inner surfaces of the viewing and the temple engaging areas away from the face of the wearer.

18. The eye cover of claim 15, wherein the flexible sheet of material includes a plurality of apertures and the bendable wire is engaged to the flexible sheet of material by being woven through the apertures, and a flexible tube covering the wire.

19. The eye cover of claim 15, wherein the flexible sheet of material includes a plurality of apertures and the bendable wire is engaged to the flexible sheet of material by being woven through the apertures, the wire having a flat ribbon shape and a flexible tube covering the wire.

20. The eye cover of claim 15, wherein the nose engaging areas has a nose receiving notch, with a nose guard engaged to the nose receiving notch and wherein the flexible sheet of material includes a plurality of apertures and the bendable wire is engaged to the flexible sheet of material by being woven through the apertures.

21. The eye cover of claim 15, wherein the flexible sheet of material includes a pair of apertures at an upper portion of the nose engaging area, and an aperture near the outer end of each temple engaging area, the bendable wire being engaged to the flexible sheet of material by being woven through the apertures.

22. The eye cover of claim 15, wherein the flexible sheet of material includes a pair of apertures at an upper portion of the nose engaging area, and an aperture near the outer end of each temple engaging area, the bendable wire being engaged to the flexible sheet of material by being woven through the apertures with opposite ends of the wire being bent from an inner to and outer surface of each temple engaging area, around a respective end of each temple engaging area and into an aperture at the end of the respective temple engaging area with a clearance between an inside of the wire bend and the end of each temple engaging area for allowing the wire to slide with respect to the flexible sheet of material when the flexible sheet of material is moved between the arcuate and storage positions.

23. An eye cover comprising: an elongated and flexible sheet of material adapted to extend horizontally over both eyes and temples of a wearer, to a location forward of the ears of the wearer, the sheet having a central nose engaging area, a pair of viewing areas on opposite sides of the nose engaging area, and a pair of temple engaging areas each extending from one of the viewing areas, at least the viewing areas being transparent, the flexible sheet of material being bent for use by the wearer, into an arcuate position with the temple engaging areas over temples of the wearer, at a location forward of the ears of the wearer; and a bendable wire engaged to the flexible sheet of material and extending across the pair of viewing areas, the nose engaging area and the pair of temple engaging areas, near an upper edge of the flexible sheet of material for being bent to form, and to resiliently maintain, the arcuate position, and for being bent to form and maintain a storage position of the flexible sheet of material which is flatter than the arcuate position, the flexible sheet of material including a plurality of apertures and the bendable wire being engaged to the flexible sheet of material by being woven through the apertures, the wire having a flat ribbon shape and a flexible tube covering the wire, the flexible sheet of material including a pair of apertures at an upper portion of the nose engaging area, and an aperture near the outer end of each temple engaging area, the bendable wire being engaged to the flexible sheet of material by being woven through the apertures with opposite ends of the wire being bent from an inner to and outer surface of each temple engaging area, around a respective end of each temple engaging area and into an aperture at the end of the respective temple engaging area with a clearance between an inside of the wire bend and the end of each temple engaging are for allowing the wire to slide with respect to the flexible sheet of material when the flexible sheet of material is moved between the arcuate and storage positions.

* * * * *